United States Patent [19]

Kasai et al.

[11] Patent Number: 5,730,787
[45] Date of Patent: Mar. 24, 1998

[54] DESENSITIZING SOLUTION FOR LITHOGRAPHY

[75] Inventors: Seishi Kasai; Ryousuke Itakura; Eiichi Kato, all of Shizuoka, Japan

[73] Assignee: Fuji Photo Film Co., Ltd., Kanagawa, Japan

[21] Appl. No.: 802,244

[22] Filed: Feb. 19, 1997

[30] Foreign Application Priority Data

Feb. 20, 1996 [JP] Japan ................... 8-032224

[51] Int. Cl.$^6$ .................................................. G03G 9/00
[52] U.S. Cl. ..................................... 106/2; 101/450.1
[58] Field of Search ........................... 106/2; 101/450.1

[56] References Cited

U.S. PATENT DOCUMENTS

| | | | |
|---|---|---|---|
| 4,579,591 | 4/1986 | Suzuki et al. | 106/2 |
| 4,734,132 | 3/1988 | Yoshida | 106/2 |
| 4,834,797 | 5/1989 | Toyofuku et al. | 106/2 |
| 4,925,761 | 5/1990 | Kulisz, Sr. et al. | 106/2 |
| 4,954,173 | 9/1990 | Yoshida | 106/2 |
| 5,525,458 | 6/1996 | Takizawa | 106/2 |
| 5,565,290 | 10/1996 | Itakura et al. | 106/2 |

FOREIGN PATENT DOCUMENTS

| | | |
|---|---|---|
| 53-109701 | 9/1978 | Japan . |
| 62-105692 | 5/1987 | Japan . |

*Primary Examiner*—Melissa Bonner
*Attorney, Agent, or Firm*—McAulay Fisher Nissen Goldberg & Kiel, LLP

[57] ABSTRACT

A desensitizing solution for lithography is disclosed which contains at least one member selected from cyclic amine and ammonium compounds each containing specific structures. The desensitizing solution does not cause environmental pollution, is stable to long-term storage, continuous use, and fluctuations in environmental conditions, is effective in reducing the time required for etching treatment, and has excellent desensitization performance.

4 Claims, No Drawings

DESENSITIZING SOLUTION FOR LITHOGRAPHY

FIELD OF THE INVENTION

The present invention relates to a desensitizing solution for lithography. More particularly, the present invention relates to a desensitizing solution for lithographic plates consisting mainly of a metal oxide, a metal sulfide, and a binder resin, e.g., electrophotographic original printing plates and direct imaging original printing plates.

BACKGROUND OF THE INVENTION

Electrophotographic lithographic original plates (hereinafter referred to as "masters") have a photosensitive layer comprising fine photoconductive particles, such as zinc oxide particles, dispersed in a resin binder, and are obtained by forming an ink-receptive image on this layer by an ordinary electrophotographic technique.

In offset printing, a plate having nonimage areas (hydrophilic areas) readily wettable by water and image areas (ink-receptive areas) sparingly wetted by water is generally used. However, in the case of electrophotographic original offset printing plates, normal printing is impossible when the printing plates are used as they are, because the printing surface of these untreated plates is made of a hydrophobic photoelectroconductive layer and a printing ink hence adheres also to nonimage areas.

It is therefore necessary to desensitize the nonimage areas of such an original printing plate prior to printing to impart hydrophilicity. Proposed so far as this kind of desensitizing solutions include a cyanide-containing desensitizing solution containing a ferrocyanate and a ferricyanate as major components and a cyanide-free desensitizing solution containing an amine/cobalt complex, phytic acid (inositol hexaphosphate), a derivative of the acid, and a guanidine derivative as major components.

However, these prior art desensitizing solutions are not wholly satisfactory. Specifically, the former desensitizing solution, which contains a ferrocyanate and a ferricyanate, has a drawback that it suffers discoloration and precipitation upon exposure to light because of the instability of ferrocyanate ions and ferricyanate ions to heat and light to come to have weakened desensitizing power, although it has high initial desensitizing power and is capable of rapidly forming a tenacious hydrophilic film. The former desensitizing solution has another drawback that since it contains cyanide (CN) ions, a free cyanide is detected in wastewater, etc. to pose various problems concerning environmental pollution.

On the other hand, the latter desensitizing solution, which is a cyanide-free solution containing desensitizing agents such as an ammine/cobalt complex, phytic acid, and guanidine as major components, was proposed in view of the drawbacks described above. However, this prior art desensitizing solution also cannot give a fully satisfactory lithographic original plate. Specifically, the latter desensitizing solution has a drawback that since it has a lower film-forming rate than the former, a hydrophilic film having high physical strength and capable of being immediately subjected to printing cannot be formed when an original plate is etched only once with the latter desensitizing solution in a processor, leading to scumming and plugging of halftone dot.

It has conventionally been well known that phytic acid and metallized derivatives thereof form metal chelate compounds, and various proposals have been made on use of these compounds as desensitizing agents for original offset printing plates. However, all these desensitizing agents have a drawback that since they have a low film-forming rate, a hydrophilic film usable in printing cannot be formed through one treating operation in a processor and the resulting film has poor ink repellency, leading to scumming and plugging of halftone dot.

For eliminating the problems described above, investigations are being made on addition of various additives to desensitizing solutions based on phytic acid.

Examples thereof include a desensitizing solution containing a combination of phytic acid and a metal complex of an aminocarboxylic acid or the like (see JP-B-2-39397; the term "JP-B" as used herein means an "examined Japanese patent publication"), a desensitizing solution containing a combination of phytic acid and a hexametaphosphate (see JP-A-62-7597), and desensitizing solutions containing a lower amine, an alkanolamine, or a polyamine (see, for example, JP-A-54-117201, JP-A-53-109701, and JP-A-1-25994; the term "JP-A" as used herein means an "unexamined published Japanese patent application"). Although these desensitizing solutions are satisfactory in water receptivity in the initial stage of use, a sufficient effect cannot be obtained therewith because they have problems, for example, that continuous use results in reduced etching and reduced water receptivity and use after long-term storage results in reduced water receptivity to cause scumming.

Desensitizing solutions containing a cationic polymer (see, for example, JP-A-60-23099) have drawbacks that continuous use and long-term storage result in a decrease in performance as in the above-described desensitizing solutions, and that they cause rusting.

Further, desensitizing solutions containing a combination of phytic acid and a polyethyleneimine copolymer have been proposed (see, for example, JP-A-7-68967 and JP-A-7-137475). However, this kind of desensitizing solutions still have problems, for example, that the latitude in which the impartation of hydrophilicity to nonimage areas by etching is consistent with the impartation of ink receptivity to image areas is narrow, or long-term continuous use results in a decrease in performance.

On the other hand, automatic printing machines especially of small size which have a desensitizing system united therewith have spread increasingly in recent years from the standpoint of labor reduction. In addition, the time required for electrophotographically produced offset masters to be processed to give finished printing plates is being reduced. Under these circumstances, a desensitizing treatment is required to be carried out rapidly and to meet the attainment of a longer life.

With respect to systems for electrophotographically producing masters, a digital exposure technique has been proposed. As a result, not only conventional masters bearing images consisting mainly of line originals and characters, but also masters bearing fine images such as middle tone images, screen tints, etc. have come to be easily produced. Although printing plates are hence required to reproduce such fine images on prints, this is difficult to attain with any of the prior art known desensitizing solutions.

SUMMARY OF THE INVENTION

An object of the present invention is to provide a desensitizing solution for offset printing plates which does not cause environmental pollution, is stable to long-term storage and continuous use, is effective in reducing the time required for etching treatment, and has excellent desensitization performance.

Another object of the present invention is to provide a desensitizing solution for offset printing which enables the production of an offset printing plate capable of satisfactorily reproducing a fine image, e.g., a middle tone image or screen tint, and of giving prints in which the nonimage areas are free from scumming.

That is, the problems described above can be eliminated by using the desensitizing solution of the present invention for etching.

The present invention provides the following desensitizing solutions.

(1) A desensitizing solution for lithography which contains at least one member selected from cyclic amine and ammonium compounds each containing at least two structures represented by general formula (I):

  (I)

wherein P" represents —$PO_3H_2$, —$OPO_3H_2$, or a salt of either.

(2) A desensitizing solution for lithography which contains at least one compound represented by general formula (II):

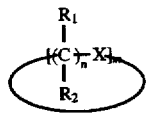  (II)

wherein X represents >$NCH_2P"$, >N—$R_3$, an oxygen atom, or a sulfur atom; P" represents —$PO_3H_2$, —$OPO_3H_2$, or a salt of either; $R_1$ and $R_2$ each represents a hydrogen atom or an optionally substituted organic residue, provided that the organic residues may be bonded to each other to form a ring; $R_3$ represents a hydrogen atom or an optionally substituted aliphatic or aromatic group having 1 to 22 carbon atoms; and n represents an integer of from 1 to 10, and m represents an integer of from 2 to 15, provided that the formula contains at least two groups represented by >$NCH_2P"$.

(3) A desensitizing solution for lithography which contains at least one compound represented by general formula (III):

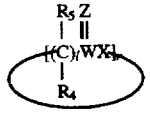  (III)

wherein Z represents an oxygen atom or a sulfur atom; W represents a carbon atom or a silicon atom; X has the same meaning as the X in general formula (II) described in (2) above; $R_4$ and $R_5$ have the same meaning as the $R_1$ and $R_2$ in general formula (II); and l has the same meaning as the n in general formula (II), and r has the same meaning as the m in general formula (II), provided that the formula contains at least two groups represented by >$NCH_2P"$.

(4) A desensitizing solution for lithography which contains at least one compound represented by general formula (IV):

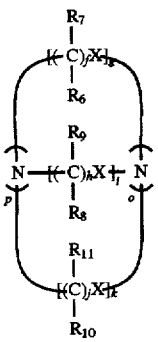  (IV)

wherein X has the same meaning as the X in general formula (II) described in (2) above; $R_6$ and $R_7$, $R_8$ and $R_9$, and $R_{10}$ and $R_{11}$ each have the same meaning as the $R_1$ and $R_2$ in general formula (II); f, h, and j each has the same meaning as the n in general formula (II); g, i, and k each has the same meaning as the m in general formula (II); and p and o each represents an integer of 1, 2, or 3, provided that the formula contains at least two groups represented by >$NCH_2P"$.

DETAILED DESCRIPTION OF THE INVENTION

Due to its specific chemical structure, the compound used in the present invention has been greatly improved in chelating reactivity and the rate of precipitate formation as compared with conventionally known compounds having chelating ability, such as phytic acid and phytic salts. This compound is presumed to produce the following effects. Hydrophilic treatment can hence be carried out at a heightened rate in a reduced time period. That is, when many original plates are treated with the desensitizing solution, the time period in which each original plate resides in the desensitizing solution is shorter than in the treatment of the same number of original plates with conventional desensitizing solutions. Moreover, the desensitizing solution of the present invention can be prevented from being contaminated with $Zn^{2+}$ ions and other substances which cause precipitation and other troubles in the solution. Consequently, the desensitizing solution of the present invention has improved long-term stability, suitability for running, etc., not to mention high desensitizing power.

The desensitizing solution of the present invention contains neither a ferrocyanate nor ferricyanate compound, which pose an environmental problem and deteriorate upon exposure to light or heat. The desensitizing solution is less influenced by fluctuations in the condition of the printing atmosphere than prior art cyanide-free desensitizing solutions. It is stable and undergoes neither discoloration nor precipitation, even when stored over a prolonged period. In addition, the desensitizing solution has a significantly improved film-forming rate. It is therefore an excellent cyanide-free desensitizing solution which, even through high-speed etching, can give original offset printing plates causing neither scumming nor plugging of halftone dot.

In general formula (I), P" represents —$PO_3H_2$ (phosphonate group), —$OPO_3H_2$ (phosphate group), or a salt of either. Preferred examples of the salt include inorganic salts (e.g., salts with lithium, sodium, and potassium); ammonium salts, salts with organic bases [e.g., primary, secondary, and tertiary amines (wherein examples of the hydrocarbon groups include methyl, ethyl, propyl, butyl, pentyl, hexyl, heptyl, octyl, decyl, dodecyl, tridecyl, tetradecyl, hexadecyl, octadecyl, cyclohexyl, cyclooctyl, benzyl, and phenetyl; these hydrocarbon groups may contain one or more substituents selected from hydroxyl, halogen atoms, cyano, alkoxy groups, amide groups, etc.), aniline and derivatives thereof (e.g., aniline, N-methylaniline, N,N-dimethylaniline, N-ethylaniline, N-butylaniline, and N-methyl-N-butylaniline), and heterocyclic nitrogen compounds (e.g., pyridine, morpholine, and piperazine)], and intramolecular salts with $=NCH_2-$ (e.g., $-N^+CH_2PO_3^-H$ and $-N^+CH_2OPO_3^-H$). In these salt compounds, part or all of the acid groups in the molecule may be in a salt form, and the salts formed may be the same or different.

In general formula (II), $R_1$ and $R_2$ each represents a hydrogen atom or an optionally substituted organic residue, provided that these organic residues may be bonded to each other to form a ring. Examples of the organic residues include optionally substituted alkyl, cycloalkyl, alkenyl, aralkyl, and aryl groups having 1 to 18 carbon atoms, alkoxy groups, sulfide groups, amino groups, halogens, cyano, nitro, hydroxy, carboxyl, a phosphonate group, a phosphate group, a sulfo group (including salts of these acid groups), amide groups, sulfonamide groups, ester groups, urea groups, and urethane groups. Examples of the substituents include alkoxy groups, sulfide groups, amino groups, halogens, cyano, nitro, hydroxy, carboxyl, a phosphonate group, a phosphate group, a sulfo group (including salts of these acid groups), amide groups, sulfonamide groups, ester groups, urea groups, and urethane groups.

$R_1$ and $R_2$ may be bonded to each other to form an optionally substituted aliphatic or aromatic ring having 3 to 22 carbon atoms.

$R_1$ and $R_2$ each preferably represents a hydrogen atom, an optionally substituted alkyl group having 1 to 14 carbon atoms (e.g., methyl, ethyl, propyl, isopropyl, butyl, isobutyl, heptyl, hexyl, octyl, decyl, dodecyl, hexadecyl, octadecyl, 2-hydroxyethyl, 2-hydroxypropyl, 3-hydroxypropyl, 4-hydroxybutyl, 2-hydroxybutyl, 2-methoxyethyl, 2-butoxyethyl, 2-ethoxyethyl, 4-methoxybutyl, methylthioethyl, methylthiobutyl, 2-aminoethyl, N,N'-dimethylaminoethyl, piperidinomethyl, pyrrolidinoethyl, 2-chloroethyl, 2-chlorobutyl, 2-bromoethyl, 2-cyanoethyl, 4-cyanobutyl, 2-carboxyethyl, carboxymethyl, 3-carboxypropyl, 3-morpholinopropyl, 2-morpholinoethyl, 2-sulfoethyl, 2-piperidinoethyl, amidomethyl, thioethyl, imidazolididoethyl, sulfonamidoethyl, phosphonopropyl, or phosphonomethylaminoethyl), an optionally substituted alkenyl group having 2 to 18 carbon atoms (e.g., vinyl, allyl, isopropenyl, butenyl, hexenyl, heptenyl, or octenyl), an optionally substituted aralkyl group having 7 to 12 carbon atoms (e.g., benzyl, phenethyl, naphthylmethyl, 2-naphthylethyl, methoxybenzyl, ethoxybenzyl, or methylbenzyl), an optionally substituted cycloalkyl group having 5 to 8 carbon atoms (e.g., cyclopentyl, cyclohexyl, or cycloheptyl), or an optionally substituted aryl group having 6 to 12 carbon atoms (e.g., phenyl, tolyl, xylyl, mesityl, naphthyl, methoxyphenyl, ethoxyphenyl, fluorophenyl, methylchlorophenyl, difluorophenyl, bromophenyl, chlorophenyl, dichlorophenyl, methylcarbonylphenyl, methoxycarbonylphenyl, ethoxycarbonylphenyl, methanesulfonylphenyl, or cyanophenyl).

Examples of the ring formed by $R_1$ and $R_2$ bonded to each other include optionally substituted aliphatic rings having 3 to 18 carbon atoms (e.g., cyclopropane, cyclobutane, cyclopentane, cyclohexane, cycloheptane, bicyclo[2.2.1]heptene, and bicyclo[2.2.2]octane) and optionally substituted aromatic rings having 6 to 12 carbon atoms (e.g., benzene, naphthalene, anthracene, pyrrole, pyridine, imidazole, and thiophene). Examples of the substituents include the same substituents enumerated hereinabove with regard to $R_1$ and $R_2$.

$R_3$ preferably represents a hydrogen atom, an optionally substituted alkyl group having 1 to 14 carbon atoms (e.g., methyl, ethyl, propyl, isopropyl, butyl, isobutyl, heptyl, hexyl, octyl, decyl, dodecyl, hexadecyl, octadecyl, 2-hydroxyethyl, 2-hydroxypropyl, 3-hydroxypropyl, 4-hydroxybutyl, 2-hydroxybutyl, 2-methoxyethyl, 2-butoxyethyl, 2-ethoxyethyl, 4-methoxybutyl, methylthioethyl, methylthiobutyl, 2-aminoethyl, N,N'-dimethylaminoethyl, piperidinomethyl, pyrrolidinoethyl, 2-chloroethyl, 2-chlorobutyl, 2-bromoethyl, 2-cyanoethyl, 4-cyanobutyl, 2-carboxyethyl, carboxymethyl, 3-carboxypropyl, 3-morpholinopropyl, 2-morpholinoethyl, 2-sulfoethyl, 2-piperidinoethyl, amidomethyl, thioethyl, imidazolididoethyl, sulfonamidoethyl, phosphonopropyl, or phosphonomethylaminoethyl), an optionally substituted alkenyl group having 2 to 18 carbon atoms (e.g., vinyl, allyl, isopropenyl, butenyl, hexenyl, heptenyl, or octenyl), an optionally substituted aralkyl group having 7 to 12 carbon atoms (e.g., benzyl, phenethyl, naphthylmethyl, 2-naphthylethyl, methoxybenzyl, ethoxybenzyl, or methylbenzyl), an optionally substituted cycloalkyl group having 5 to 8 carbon atoms (e.g., cyclopentyl, cyclohexyl, or cycloheptyl), or an optionally substituted aryl group having 6 to 12 carbon atoms (e.g., phenyl, tolyl, xylyl, mesityl, naphthyl, methoxyphenyl, ethoxyphenyl, fluorophenyl, methylchlorophenyl, difluorophenyl, bromophenyl, chlorophenyl, dichlorophenyl, methylcarbonylphenyl, methoxycarbonylphenyl, ethoxycarbonylphenyl, methanesulfonylphenyl, or cyanophenyl).

$R_4$ and $R_5$, $R_6$ and $R_7$, $R_8$ and $R_9$, and $R_{10}$ and $R_{11}$ each have the same meaning as the $R_1$ and $R_2$ described hereinabove.

Specific examples of the compounds represented by general formulae (I) to (IV) for use in the present invention are given below. It should, however, be noted that the scope of the present invention is not limited by these.

In the following exemplified compounds, $P_1$ represents a methyl phosphonate group ($-CH_2PO_3H_2$) and $P_2$ represents a methyl phosphate group ($-CH_2OPO_3H_2$).

1.

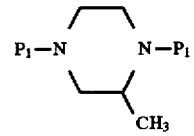

2.

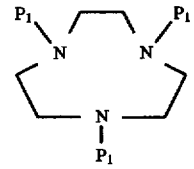

3.

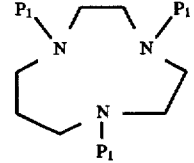

4.

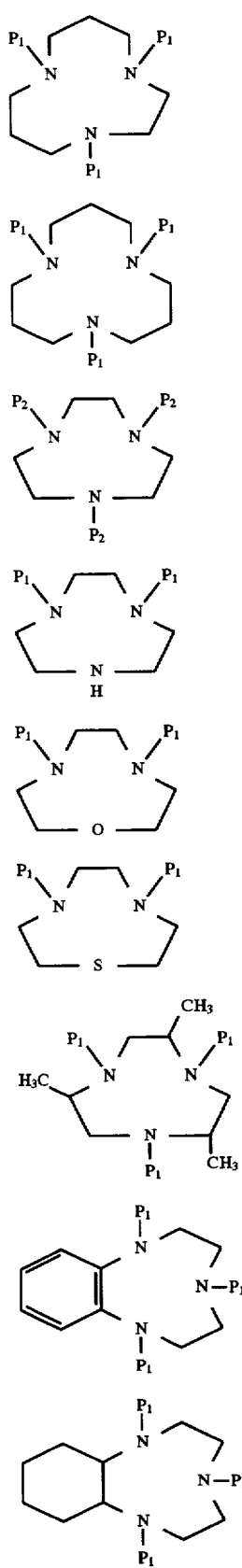
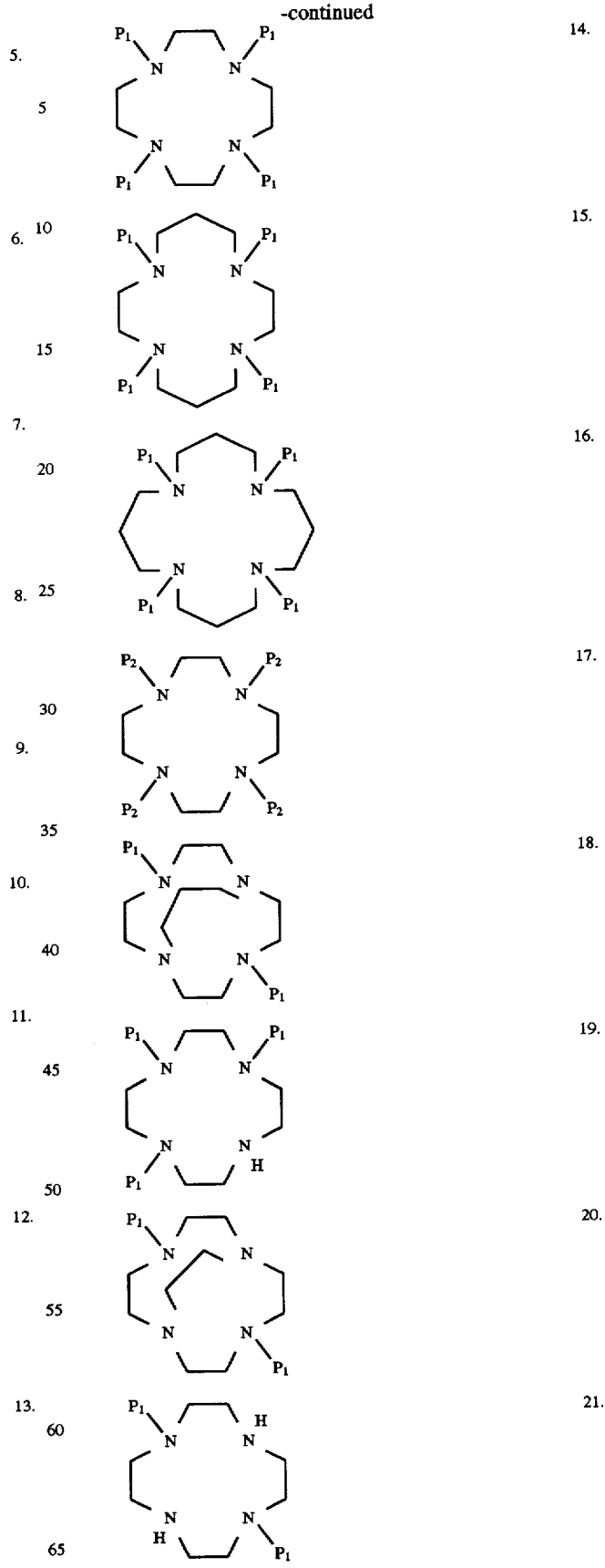

-continued
22. 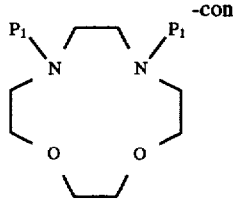
23. 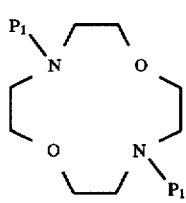
24. 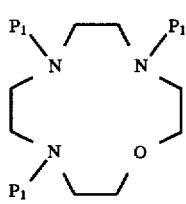
25. 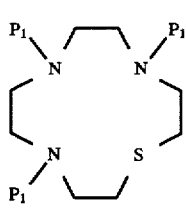
26. 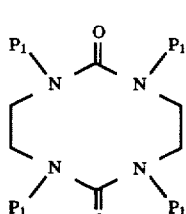
27. 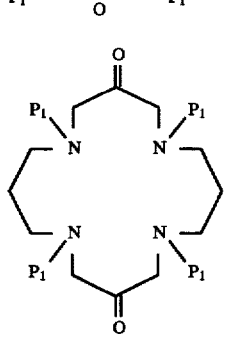
28. 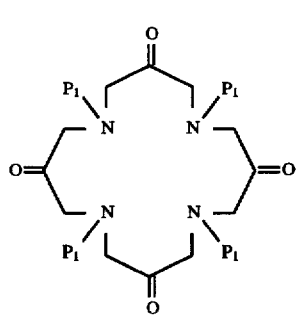
-continued
29. 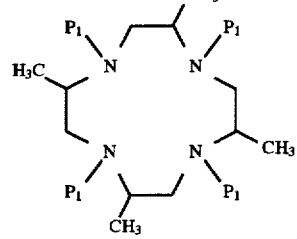
30. 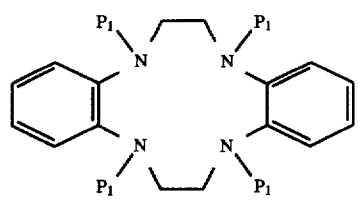
31. 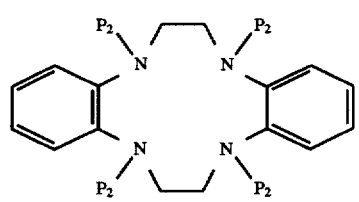
32. 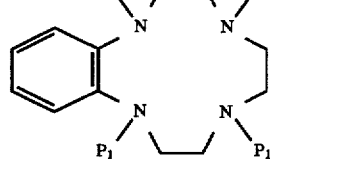
33. 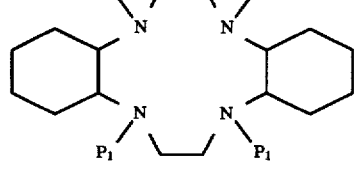
34. 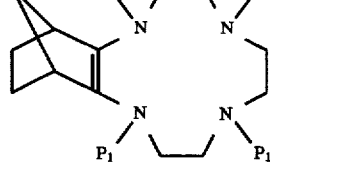
35. 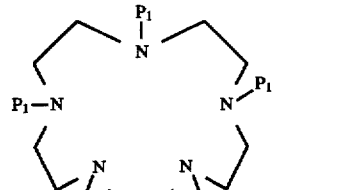

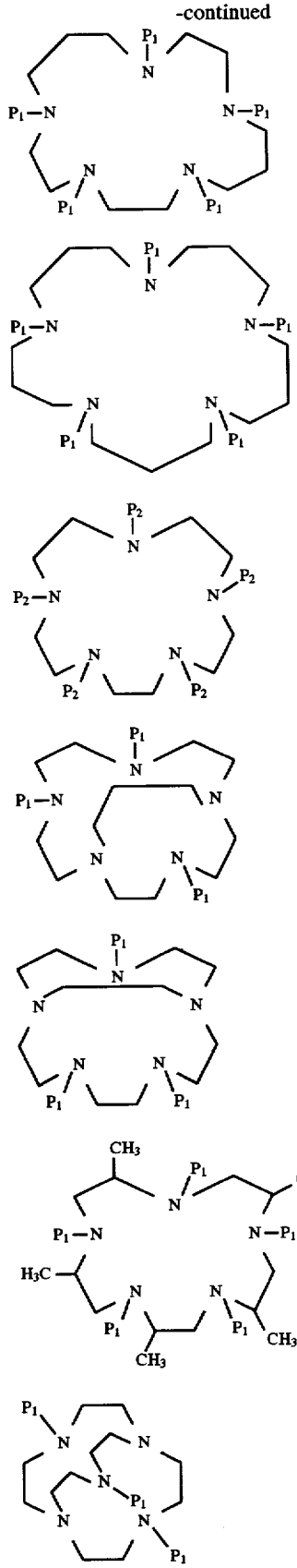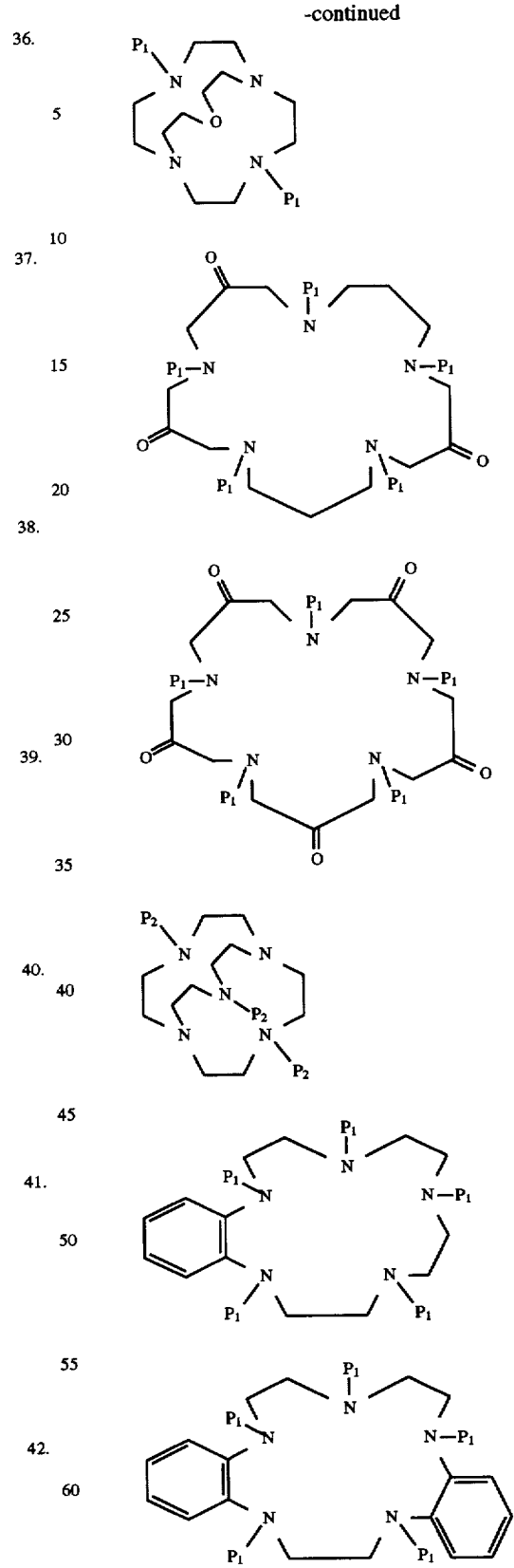

49.
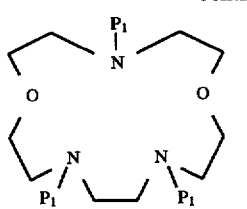
50.
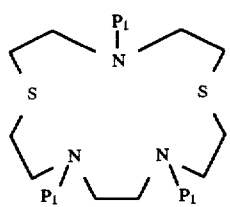
51.
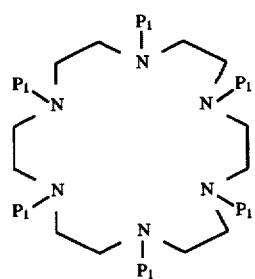
52.
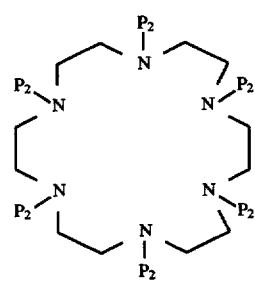
53.
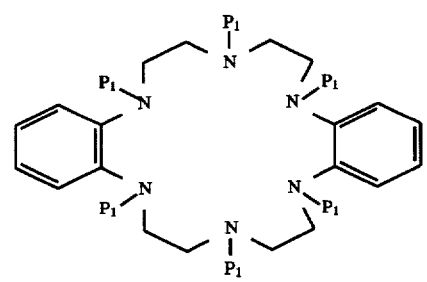
54.
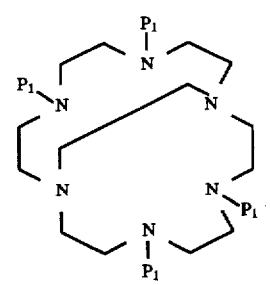
55.
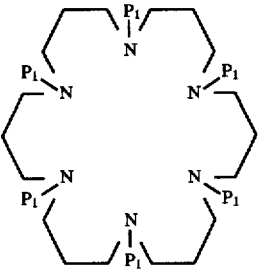
56.
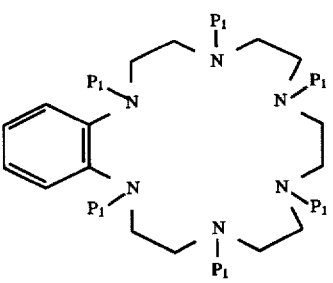
57.
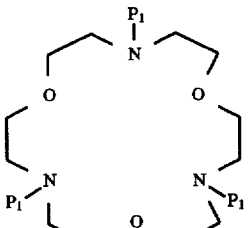
58.
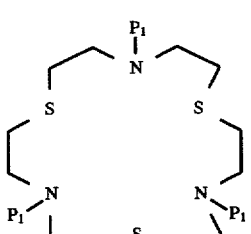
59.
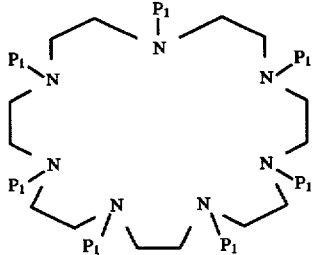
60.
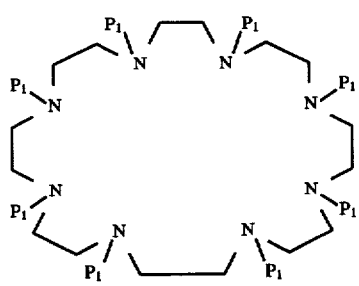

-continued

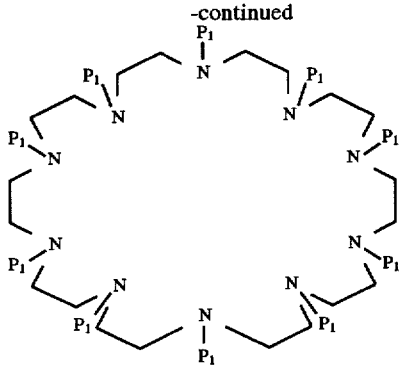

61.

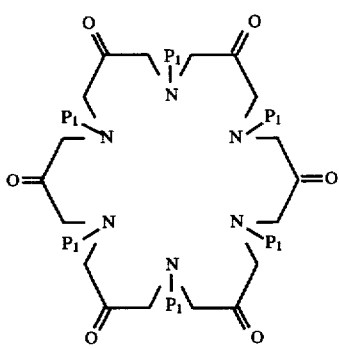

62.

The compounds for use in the present invention can be synthesized, for example, by the addition reaction of phosphonic acid with a Schiff base as described in *Synthesis*, 81–96 (1979) and *Jikken Kagaku Koza* (*Lectures on Experimental Chemistry*) 19, (published by Maruzen, Japan, 1957), or by the dehydrating condensation reaction of an alcohol with orthophosphoric acid or the condensation reaction of an alcohol with a phosphorus oxychloride.

In the desensitizing solution of the present invention, the amount of one or more compounds according to the invention which are capable of forming a chelate with a zinc ion is from 10 to 300 parts by weight, preferably from 30 to 100 parts by weight, per 1,000 parts by weight of the desensitizing solution. The compounds according to the present invention may be used alone or in combination of two or more thereof.

One or more of those compounds are dissolved in ion-exchanged water or tap water to give a desensitizing solution of the present invention. Besides the ingredients described above, the desensitizing solution may further contain suitable amounts of pH regulators such as organic or inorganic acids and basic hydroxides, e.g., potassium hydroxide and sodium hydroxide, wetting agents such as ethylene glycol, sorbitol, glycerol, gum arabic, dipropylene glycol, dimethylacetamide, hexylene glycol, butanediol, butyl Cellosolve, and surfactants, antiseptics such as salicylic acid, phenol, butyl p-benzoate, sodium dehydroacetate, 4-isothiazolin-3-one compounds, 2-bromo-2-nitro-1,3-propanediol, and chloroacetamide, and rust preventives such as EDTA, pyrophosphoric acid, metaphosphoric acid, hexametaphosphoric acid, and 2-mercaptobenzimidazole.

Before being used, the desensitizing solution is preferably regulated so as to have a pH of from 3 to 6. The desensitizing solution of the present invention can also be used as a fountain solution after being diluted with water.

The present invention will be explained below in more detail by reference to the following Examples, but the invention should not be construed as being limited thereto.

EXAMPLE 1

| | |
|---|---|
| Water | 1,000 parts by weight |
| Aza-18-crown-6-hexa(methylenephosphonic acid) (Compound No. 51) | 80 parts by weight |

EXAMPLE 2

A system having the same composition as in Example 1, except that the compound used in Example 1 was replaced with aza-15-crown-5-pentakis(methylenephosphonic acid) (Compound No. 35).

EXAMPLE 3

A system having the same composition as in Example 1, except that the compound used in Example 1 was replaced with 1,4,8,11-tetraazacyclotetradecatetrakis (methylenephosphonic acid) (Compound No. 15).

EXAMPLE 4

A system having the same composition as in Example 1, except that the compound used in Example 1 was replaced with benzoaza-18-crown-6-hexa(methylenephosphonic acid) (Compound No. 56).

COMPARATIVE EXAMPLE A

A system having the same composition as in Example 1, except that the compound used in Example 1 was replaced with phytic acid.

COMPARATIVE EXAMPLE B

A system having the same composition as in Example 1, except that the compound used in Example 1 was replaced with EDTA.

COMPARATIVE EXAMPLE C

A system having the same composition as in Example 1, except that the compound used in Example 1 was replaced with phosphonomethylimidinoacetic acid.

COMPARATIVE EXAMPLE D

A system having the same composition as in Example 1, except that the compound used in Example 1 was replaced with phenylphosphonic acid.

Each compound was completely dissolved. KOH was added to each resulting solution to adjust the pH thereof to 4.3.

These solutions were evaluated through actual printing, and the results obtained are shown in Table 1.

TABLE 1

| Evaluation Item | Scumming (note 1) | | Inking Property (note 2) | | Suitability for Running (note 3) | Long-term Stability (note 4) |
|---|---|---|---|---|---|---|
| Environmental Conditions | I 25° C./60% RH | II 35° C./80% RH | I | II | | |
| Example 1 | o | o | o | o | o good | o good |
| Example 2 | o | o | o | o | o good | o good |
| Example 3 | o | Δ | o | o | o good | o good |
| Example 4 | o | Δ | o | o | Δ slight scumming | o good |
| Comparative Example A | Δ | x | Δ | o | x precipitation | x deterioration due to scumming |
| Comparative Example B | xx | xx | o | o | xx scumming | — no change |
| Comparative Example C | x | x | x | Δ | x precipitation | xx deterioration due to scumming |
| Comparative Example D | xx | xx | o | o | xx scumming | — no change |

The properties shown in Table 1 were evaluated by the following methods.

(Note 1) Scumming:

Sensitive material ELP-Ix (plate material comprising a paper support and a photoelectroconductive layer (ZnO/binder dispersion) formed thereon) and fully automatic platemaking machine ELP404V (manufactured by Fuji Photo Film Co., Ltd.) were allowed to stand for a whole day and night at ordinary temperature and humidity (20° C., 65%). Thereafter, original printing plates bearing a copied image were produced. The original plates obtained were treated respectively with the desensitizing solutions prepared in Examples 1 to 4 and Comparative Examples A to D, by passing each original plate once through an etching machine containing the desensitizing solution under the environmental conditions shown in Table 1.

Each of the resulting printing plates was subjected to printing using printing machine Hamada 611XLA-II (manufactured by Hamada K.K., Japan) and a fountain solution prepared by diluting the desensitizing solution obtained in Example 1 with distilled water five times. The hundredth print obtained was visually evaluated for scumming, wherein o showed no scumming, xx showed scumming on the whole non-image part, and Δ and x were between o and xx.

(Note 2) Inking Property:

Original printing plates were produced in the same manner as for the evaluation of scumming. The original plates obtained were treated respectively with the desensitizing solutions prepared in Examples 1 to 4 and Comparative Examples A to D, by passing each original plate once through an etching machine containing the desensitizing solution under the environmental conditions shown in Table 1. Each of the resulting plates was subjected to printing in the same manner as for the evaluation of scumming, and the tenth print obtained was visually evaluated for inking property in the screen tint part, wherein o showed that the image part was clearly reproduced, x showed that many clears occurred on the image part, and Δ was between o and x.

(Note 3) Suitability for Running:

Original printing plates were produced in the same manner as for the evaluation of scumming. With respect to each of the desensitizing solutions prepared in Examples 1 to 4 and Comparative Examples A to D, two thousand original plates thus obtained were treated therewith by passing the original plates once through an etching machine containing the desensitizing solution.

Each resulting two thousandth plate was subjected to printing and evaluated for scumming in the same manner as for the evaluation of scumming (Note 1). Further, each desensitizing solution was evaluated for any abnormality, e.g., precipitation.

(Note 4) Long-term Stability:

The desensitizing solutions prepared in Examples 1 to 4 and Comparative Examples A to D were allowed to stand under high-temperature conditions (50° C., 80% RH) for 2 weeks. Thereafter, original printing plates were produced in the same manner as for the evaluation of scumming (Note 1), and were then treated respectively with the desensitizing solutions by passing each original plate once through an etching machine containing the desensitizing solution. The resulting printing plates were subjected to printing and evaluated for scumming in the same manner as for the evaluation of scumming (Note 1).

The desensitizing solutions of Examples 1 to 4 according to the present invention were satisfactory in both scumming and inking property, and were clearly superior in these performances to the desensitizing solutions of Comparative Examples A, B, and C.

With respect to suitability for running, the desensitizing solutions of Comparative Examples A and C developed a precipitate to show impaired performances. In contrast, the desensitizing solutions according to the present invention were free from precipitation or any other abnormality even after 2,000-plate running, and retained the same performances as the initial ones. Further, the desensitizing solutions according to the present invention had better long-term stability than the desensitizing solutions of Comparative Examples A to D, showing that they sufficiently withstood long-term storage.

As demonstrated above, the desensitizing solutions according to the present invention were the only desensitizing solutions which withstood environmental conditions, continuous use, and long-term storage and caused no scumming.

EXAMPLES 5 TO 22

Desensitizing solutions were prepared in the same manner as in Example 1, except that the compounds shown in Table 2 were used in place of the compound in Example 1 in the respective amounts shown in the table. These desensitizing solutions were evaluated for the same properties as in Example 1.

TABLE 2

| Example No. | Compound of the invention (Exemplified Compound No.) | Amount (parts by weight) |
|---|---|---|
| 5 | 51 | 40 |
| 6 | 51 | 60 |
| 7 | 51 | 100 |
| 8 | 37 | 40 |
| 9 | 37 | 60 |
| 10 | 37 | 100 |
| 11 | 3 | 80 |
| 12 | 14 | 80 |
| 13 | 17 | 80 |
| 14 | 27 | 80 |
| 15 | 32 | 80 |
| 16 | 37 | 80 |
| 17 | 39 | 80 |
| 18 | 47 | 80 |
| 19 | 52 | 80 |
| 20 | 53 | 80 |
| 21 | 59 | 80 |
| 22 | 60 | 80 |

The desensitizing solutions of Examples 5 to 22 were satisfactory in all of scumming, inking property, stability to environmental changes, suitability for running, and long-term stability as in Example 1.

EXAMPLES 23 TO 38

Desensitizing solutions were prepared in the same manner as in Example 1, except that two or more compounds according to the present invention were used in combination as shown in Table 3 in a constant amount of 80 parts by weight. These desensitizing solutions were evaluated for scumming, inking property, suitability for running, and long-term stability in the same manner as in Example 1.

TABLE 3

| Example No. | Compounds used in Combination (Exemplified Compounds Nos.) [wt %] |
|---|---|
| 23 | (51)/(37) = 50/50 |
| 24 | (57)/(37) = 25/75 |
| 25 | (51)/(37) = 75/25 |
| 26 | (51)/(15) = 50/50 |
| 27 | (37)/(14) = 50/50 |
| 28 | (37)/(59) = 50/50 |
| 29 | (51)/(37)/(59) = 25/25/50 |
| 30 | (3)/(12)/(53) = 25/25/50 |
| 31 | (3)/(16)/(60) = 25/25/50 |
| 32 | (3)/(16)/(51) = 25/25/50 |
| 33 | (12)/(17)/(52) = 25/25/50 |
| 34 | (1)/(15)/(56) = 25/25/50 |
| 35 | (33)/(34)/(46)/(48) = 25/25/25/25 |
| 36 | (2)/(6)/(46)/(48) = 25/25/25/25 |
| 37 | (5)/(10)/(48)/(59) = 25/25/25/25 |
| 38 | (7)/(20)/(46)/(52) = 25/25/25/25 |

The desensitizing solutions of Examples 23 to 38 were satisfactory in all of scumming, inking property, stability to environmental changes, suitability for running, and long-term stability as in Example 1. The results show that combinations of two or more compounds according to the present invention could be used without posing any problem.

EXAMPLES 39 TO 45

Desensitizing solutions were prepared by adding the various wetting agents, antiseptics, and rust preventives shown in Table 4 to the same desensitizing solution as in Example 1. These desensitizing solutions were evaluated for various performances in the same manner as in Example 1.

TABLE 4

| Example No. | Wetting agent (g) | Antiseptic (mg) | Rust preventive (g) |
|---|---|---|---|
| 39 | ethylene glycol (10) | salicylic acid (100) | EDTA (2) |
| 40 | ethylene glycol (10) | salicylic acid (100) | metaphosphoric acid (2) |
| 41 | ethylene glycol (10) | salicylic acid (100) | 2-mercaptobenz-imidazole (2) |
| 42 | ethylene glycol (10) | sodium dehydroacetate (100) | EDTA (2) |
| 43 | gum arabic (10) | salicylic acid (100) | EDTA (2) |
| 44 | dimethyl acetamide (10) | salicylic acid (100) | EDTA (2) |
| 45 | butyl Cellosolve (10) | salicylic acid (100) | EDTA (2) |

The desensitizing solutions of Examples 39 to 45 were satisfactory in all of scumming, inking property, stability to environmental changes, suitability for running, and long-term stability as in Example 1. The results show that the performances of the desensitizing solution of the present invention were not influenced by the addition of the various additives.

EXAMPLE 46

A desensitizing solution containing a compound according to the present invention was diluted and used as a fountain solution to conduct a printing durability test. For master desensitization, the desensitizing solution of Example 1 was used.

The fountain solution used was prepared by diluting the desensitizing solution of Example 1 with distilled water five times.

COMPARATIVE EXAMPLE E

A fountain solution prepared by diluting the desensitizing solution of Comparative Example A with distilled water five times was used.

COMPARATIVE EXAMPLE F

A fountain solution prepared by diluting the desensitizing solution of Comparative Example C with distilled water five times was used.

The results of evaluations in Example 46 and Comparative Examples E and F are shown in Table 5.

TABLE 5

| Evaluation Item | Example 46 | Comparative Example E | Comparative Example F |
|---|---|---|---|
| Scumming of Printed Matter | no scumming throughout 5,000 prints | scumming occurred in the 2,000th print | scumming occurred in the 1,000th print |

The desensitizing solution of the present invention caused no scumming in contrast to the desensitizing solutions of Comparative Examples E and F, showing that the desensitizing solution of the present invention had high performance also as a fountain solution.

According to the present invention, a desensitizing solution for lithography can be provided which does not cause environmental pollution, is stable to long-term storage, continuous use, and fluctuations in environmental conditions, is effective in reducing the time required for etching treatment, and has excellent desensitization performance. Further, the desensitizing solution of the present invention, when suitably diluted with water, can be effectively used also as a fountain solution.

While the invention has been described in detail and with reference to specific embodiments thereof, it will be apparent to one skilled in the art that various changes and modifications can be made therein without departing from the spirit and scope thereof.

What is claimed is:

1. A desensitizing solution for lithography which contains at least one member selected from cyclic amine and ammonium compounds each containing at least two structures represented by general formula (I):

(I)

wherein P" represents $-PO_3H_2$, $-OPO_3H_2$, or a salt of either.

2. A desensitizing solution for lithography which contains at least one compound represented by general formula (II):

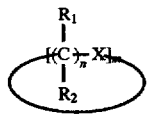
(II)

wherein X represents $>NCH_2P"$, $>N-R_3$, an oxygen atom, or a sulfur atom; P" represents $-PO_3H_2$, $-OPO_3H_2$, or a salt of either; $R_1$ and $R_2$ each represents a hydrogen atom or an optionally substituted organic residue, provided that the organic residues may be bonded to each other to form a ring; $R_3$ represents a hydrogen atom or an optionally substituted aliphatic or aromatic group having 1 to 22 carbon atoms; and n represents an integer of from 1 to 10, and m represents an integer of from 2 to 15, provided that the formula contains at least two groups represented by $>NCH_2P"$.

3. A desensitizing solution for lithography which contains at least one compound represented by general formula (III):

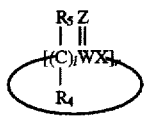
(III)

wherein Z represents an oxygen atom or a sulfur atom; W represents a carbon atom or a silicon atom; X represents $>NCH_2P"$, $>N-R_3$, an oxygen atom, or a sulfur atom; P" represents $-PO_3H_2$, $-OPO_3H_2$, or a salt of either; $R_3$ represents a hydrogen atom or an optionally substituted aliphatic or aromatic group having 1 to 22 carbon atoms; $R_4$ and $R_5$ each represents a hydrogen atom or an optionally substituted organic residue, provided that the organic residues may be bonded to each other to form a ring; and l represents an integer of from 1 to 10, and r represents an integer of from 2 to 15, provided that the formula contains at least two groups represented by $>NCH_2P"$.

4. A desensitizing solution for lithography which contains at least one compound represented by general formula (IV):

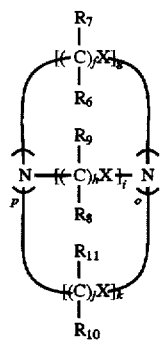
(IV)

wherein X represents $>NCH_2P"$, $>N-R_3$, an oxygen atom, or a sulfur atom; P" represents $-PO_3H_2$, $-OPO_3H_2$, or a salt of either; $R_3$ represents a hydrogen atom or an optionally substituted aliphatic or aromatic group having 1 to 22 carbon atoms; $R_6$ and $R_7$, $R_8$ and $R_9$, and $R_{10}$ and $R_{11}$ each represent a hydrogen atom or an optionally substituted organic residue, provided that the organic residues may be bonded to each other to form a ring; f, h, and j each represents an integer of from 1 to 10; g, i, and k each represents an integer of from 2 to 15; and p and o each represents an integer of 1, 2, or 3, provided that the formula contains at least two groups represented by $>NCH_2P"$.

* * * * *